United States Patent [19]

Chikama

[11] Patent Number: 4,770,188

[45] Date of Patent: Sep. 13, 1988

[54] GUIDE TUBE ASSEMBLY FOR AN ENDOSCOPE

[75] Inventor: Toshio Chikama, Tokyo, Japan

[73] Assignee: Machida Endoscope Co., Ltd., Tokyo, Japan

[21] Appl. No.: 379,323

[22] Filed: May 18, 1982

Related U.S. Application Data

[63] Continuation of Ser. No. 159,822, Jun. 16, 1980, abandoned.

[30] Foreign Application Priority Data

Jun. 30, 1979 [JP] Japan .............................. 54-090733

[51] Int. Cl.⁴ .............................................. A61B 5/00
[52] U.S. Cl. ....................................... 128/772; 604/93
[58] Field of Search ........................................ 128/4–8, 128/772; 138/134; 604/93, 104

[56] References Cited

U.S. PATENT DOCUMENTS

| | | | |
|---|---|---|---|
| 1,590,666 | 6/1926 | Angell | 138/134 |
| 3,572,325 | 3/1971 | Bazell et al. | 128/6 |
| 3,583,393 | 6/1971 | Takahashi | 128/4 |
| 3,670,721 | 6/1972 | Fukami et al. | 128/6 |
| 3,998,216 | 12/1976 | Hosano | 128/6 |
| 4,108,211 | 8/1978 | Tanaka | 128/4 |

FOREIGN PATENT DOCUMENTS

| | | | |
|---|---|---|---|
| 684492 | 1/1950 | United Kingdom | 128/6 |
| 1231015 | 5/1971 | United Kingdom | 128/6 |

*Primary Examiner*—Max Hindenburg
*Attorney, Agent, or Firm*—Peter L. Berger

[57] ABSTRACT

A guide tube assembly for an endoscope is disclosed which is usually flexible and which can be stiffened when necessary.

The assembly comprises a flexible body which is usually flexible because its components are separable from each other, while the assembly can be stiffened when necessary by drawing the components together and a porous tube of fluorocarbon is inserted in the flexible body joining the forward ends of the components together.

Usually, the assembly can freely be bent. But, the assembly can be stiffened by pulling the rear end of the porous tube for drawing the components together when necessary.

In this way, the assembly can pass through the circuitous path of the body cavity with an endoscopic instrument, while it can fix the distal end of the endoscopic instrument in position toward an object to be observed for inspection.

7 Claims, 3 Drawing Sheets

GUIDE TUBE ASSEMBLY FOR AN ENDOSCOPE

This is a continuation of application Ser. No. 159,822, filed June 16, 1980, now abandoned.

BACKGROUND OF THE INVENTION

A. Field of the Invention

The present invention relates to a guide tube assembly for an endoscope or more particularly, to a assembly which is usually flexible, which can be stiffened when necessary.

B. Description of the Prior Art

An endoscope is an optical instrument which utilizes flexible optical bundles and a flexible sheath for inspecting a body cavity or a reactor pile. When inserting the forward end and the sheath into the cavity, it is desirable that the forward end and the sheath be freely curved so that these portions can pass through the circuitous passages of the body cavity and the reactor pile. It is preferable that the forward end be fixed firmly when conducting an inspection of an object to be observed because the stable image of the object can be transmitted by the endoscope. It is desired that such a fixing function is assigned to the guide tube assembly which is used with the endoscope rather than assigning the function to the endoscope itself, because the construction of the endoscope can be simplified. In addition, such a guide tube assembly can prevent the wall of the body cavity from injury. But, such a guide tube assembly with the ability to fix the forward end has not yet been developed.

SUMMARY OF THE INVENTION

Accordingly, it is a primary object of the present invention to provide a guide tube assembly which is usually flexible but which can be stiffened when necessary.

It is another object of the invention to provide a guide tube assembly which is used for fixing means with simpliest construction.

It is further object of the invention to provide a guide tube assembly whose frictioal resistance is small.

To achieve the objects, the guide tube assembly according to the present invention comprises a flexible body which normally is flexible because its components are separated from each other, but which can be stiffened when necessary by drawing the components together and a porous tube of fluorocarbon elastomer which is inserted into the flexible body joining the forward ends of the components together.

Usually, the assembly can freely be bent. But, the assembly can be stiffened by pulling the rear end of the porous tube for contracting the components when necessary.

The above and further objects and novel features of the invention will more fully appear from the following detailed description when the same is read in connection with the accompanying drawings. It is to be expressly understood, however, that the drawings are for purpose of illustration only and are not intended as a definition of the invention.

DETAILED DESCRIPTION OF PREFERRED EMBODIMENTS

Figure 1:
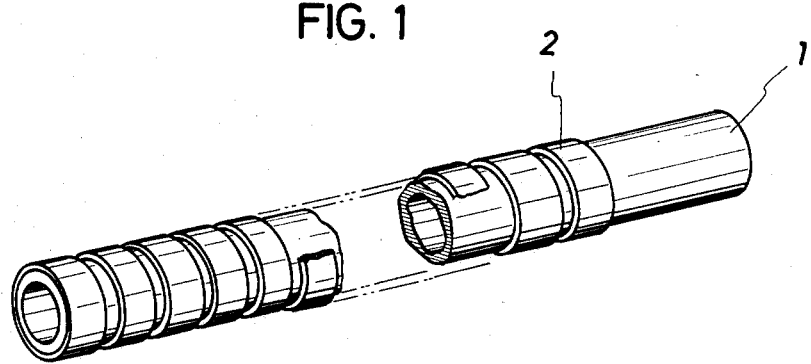
FIG. 1 is a schematic illustration showing an embodiment of a guide tube assembly according to the present invention.
Figure 2:
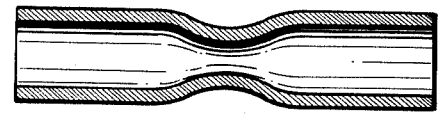
FIG. 2 is a cross-sectional view in which an ordinary tube of plastic resin is stretched.

Referring now to FIG. 1, numeral 1 indicates a porous tube of fluoric resin and numeral 2 indicates a flexible body of thin metal plate spirally wound around the porous tube 1. By way of examples of fluorocarbon elastomer, polytetrafluor ethylene, polychlorotrifluoroethylene and polyfluorethylenepropylene may be adopted. The porous tube 1 is flexible and is hardly stretched by applying a tension force in its axial direction. In addition, the porous tube 1 keeps its tubular cross section even when it is bent in a complicated body cavity. Further, the coefficient of friction of the porous tube 1 is so small that the endoscope can be smoothly inserted therein. An ordinary tube of plastic resin, such as shown in FIG. 2, is easily stretched and at the same time the diameter of the porous tube is reduced. Therefore, the distal end of a endoscope can not be inserted in the ordinary tube when the tensile force is applied to the tube. In addition, the ordinary tube will easily break when it is pulled too hard. Therefore, it can not be adapted for the guide tube assembly according to the present invention. But, the porous tube 1 of fluorocarbon elastomer has enough tensile strength that it will not break or be constricted.

Figure 3:
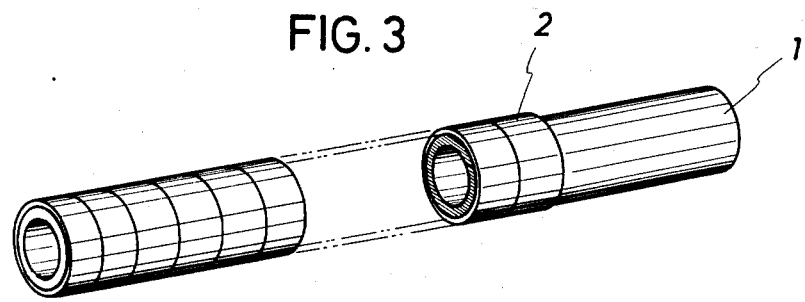
FIG. 3 is an illustration showing how the assembly of FIG. 1 is contracted.
Figure 4:
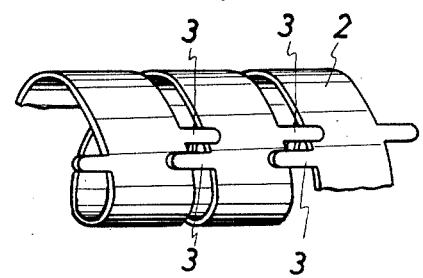
FIG. 4 is an enlarged schematic illustration of a flexible body which has projections.

Flexible body 2 which is slidably curved on the porous tube 1 is usually flexible because the components i.e. windings of the spiral are separated from each other. But, as shown in FIG. 3, the flexible body 2 will be stiffened as if it were a pipe when the spirals are drawn to by pulling the rear end of the porous tube 1. Uniform flexibility of the flexible body 2 can be obtained by the spirals because the distance between the components is averaged. For this reason, the spiral type embodiment is of great advantage when the guide tube is of long length. For locating each of the spirals and raising the combined force in case the spirals are constricted, a plurality of projections 3 in the axial direction of the components of the flexible body 2 may be provided, as shown in FIG. 4.

The flexible body 2 may be composed of a wire spirally wound around the porous tube 1. In case the guide tube assembly is used with a surgical endoscope, a cover of plastic resin such as urethane should be provided around the flexible body 2.

Figure 5:
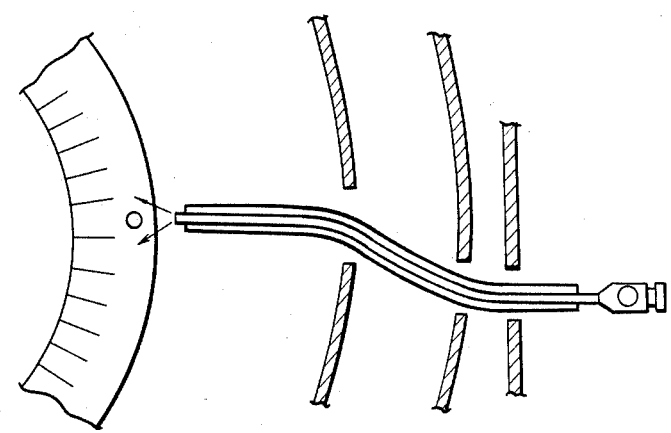
FIG. 5 is an illustration showing how the guide tube assembly according to the present invention is used.
Figure 6:
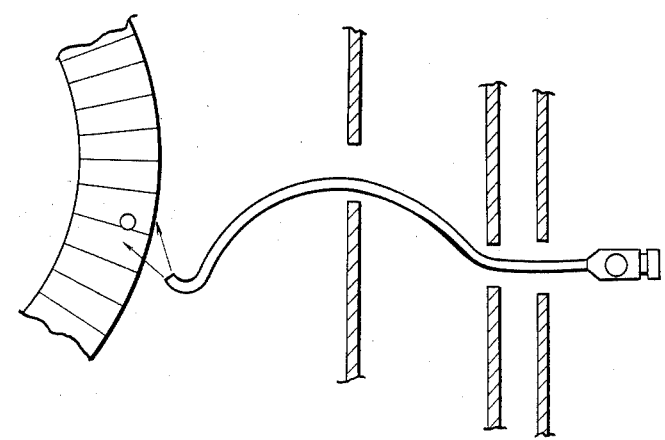
FIG. 6 is another illustration in which the guide tube assembly is not used with the endoscopic instrument.

In operation, the distal end and the flexible sheath portion of the endoscope are inserted in the porous tube 1 and, as shown in FIG. 5, they are introduced in the complicated body cavity or a reactor pile. The flexible body 2 can be freely bent because the components are separated from each other and is guided by the angle mechanism of the endoscope for smoothly introducing the endoscope into the body cavity. Upon reaching the distal examining position which is near the object to be observed, an observing window and an illumination port should be firmly fixed toward the object in order to transmit a stable image of the objection. The operator pulls the rear end of the porous tube 1 for drawing the components of flexible body 2 together by sliding the components along the porous tube 1. Then, the flexible body 2 becomes stiff as if it were a pipe and the distal examining end is firmly fixed for conducting the observation. It follows that the deviation of the observing point such as is shown in FIG. 6 can be prevented. For extracting the endoscope after completing the observation, each of the components of the flexible body 2 should be separated from each other so that the guide tube assembly may become flexible again.

As described above, the guide tube assembly according to the present invention is characterized in that it comprises a flexible body which is usually flexible because its components are separated from each other, while it can be stiffened when necessary by drawing the components together and the porous tube fluorocarbon elastomer which is inserted in the flexible body, joining the forward ends of the components together. The assembly can freely be bent, while it can be stiffened by pulling the rear end of the porous tube for drawing the components together when necessary. Accordingly, the assembly can pass through a circuitous path of a body cavity with the endoscope, while the distal end of the endoscope can be fixed toward the object for inspection.

Figure 7:
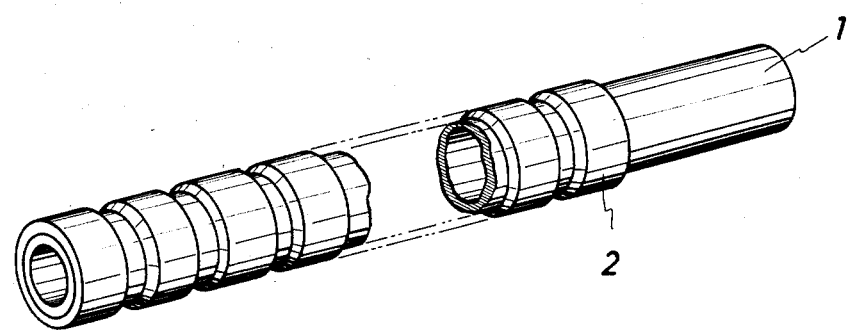
FIG. 7 is a schematic illustration showing another embodiment of the guide tube assembly according to the present invention.
Figure 8:
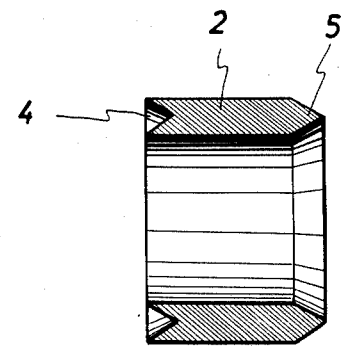
FIG. 8 is an enlarged cross-sectional view of a ring.
Figure 9:
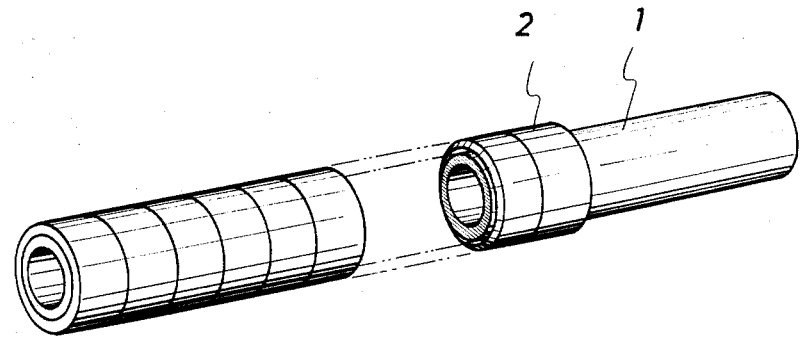
FIG. 9 is an illustration showing how the guide tube assembly of FIG. 7 is used.

Referring now to FIG. 7, another embodiment according to the present invention is shown in which the flexible body 2 is formed of a plurality of rings are provided around the porous tube 1. A groove 4 and a protrusion 5 may be provided at the axial ends of the rings. The embodiment is suitable for the guide tube assembly of relatively shorter length as the rings may come together in a limited portion of the porous tube 1. To avoid such defect, the rings may be made of magnets so that they may repel one another to average their distances. In this way, the assembly can pass through with the in the circuitous path and, as shown in FIG. 9, the assembly can be stiffened as if it were a pipe by pulling the rear end of the porous tube 1 for fixing the distal examining end of the endoscope.

While there have been shown and described the fundamental novel features of the present invention as applied to preferred embodiments, it will be understood, however, that the various omissions and substitutions and changes in the form and details may be made by those skilled in the art without departing from the spirit of the invention.

What is claimed is:

1. A guide tube assembly through which an endoscope is to be inserted with the guide tube assembly and endoscope to be inserted into a body said guide tube assembly comprising:
    a porous tube of a tubular shape formed of a material capable of being stretched axially without deformation of said tubular shape and capable of being bent without deforming said tubular shape, said tube having a forward end,
    a body comprising separable wound sections would around said porous tube, said separable wound sections axially movable along said porous tube, said separable wound sections being drawn together toward said forward end when said porous tube is stretched axially in a configuration to form a stiff body conforming to the configuration of the porous tube to fix the guide tube assembly in said configuration, said separable wound sections normally being separated from each other to enable said body to be flexible to be able to assume said configuration.

2. The guide tube according to claim 1, wherein said body comprises a thin metal plate spirally wound around said porous tube to form said separable sections as said thin metal plate is axially elongated.

3. The guide tube according to claim 1, wherein each of said sections comprises a projection provided in the axial direction for interconnecting said sections of said body.

4. The guide tube according to claim 1, wherein said separable wound sections are composed of a wire spirally wound around said porous tube.

5. The guide tube according to claim 1, wherein said separable sections are composed of rings separable from each other.

6. The guide tube according to claim 5, wherein each of said rings is magnetized to maintain an average distance between said rings on said tube.

7. A guide tube according to claim 1, wherein said material of said porous tube comprises a fluorocarbon elastomer.

* * * * *